(12) United States Patent
Ohta et al.

(10) Patent No.: US 6,855,122 B1
(45) Date of Patent: Feb. 15, 2005

(54) BLOODLESS TREATING DEVICE

(75) Inventors: Tomio Ohta, 22-31, Tezukayama 1-chome, Abeno-ku, Osaka-shi, Osaka 545-0037 (JP); Tetsuya Miyatake, Shizuoka (JP); Yoshihiko Kinoshita, Tokyo (JP)

(73) Assignees: Tomio Ohta, Osaka (JP); Nikkiso Co., Ltd., Tokyo (JP)

( * ) Notice: Subject to any disclaimer, the term of this patent is extended or adjusted under 35 U.S.C. 154(b) by 0 days.

(21) Appl. No.: 09/913,248

(22) PCT Filed: Feb. 9, 2000

(86) PCT No.: PCT/JP00/00696

§ 371 (c)(1),
(2), (4) Date: Jan. 10, 2002

(87) PCT Pub. No.: WO00/47251

PCT Pub. Date: Aug. 17, 2000

(30) Foreign Application Priority Data

Feb. 10, 1999 (JP) .............................................. 11-032631

(51) Int. Cl.$^7$ .............................................. A61M 37/00
(52) U.S. Cl. ..................... 604/6.13; 604/4.01; 604/6.15; 422/46
(58) Field of Search ........................ 604/4–6, 6.01–6.07, 604/6.11, 6.13, 6.1, 6.16, 6.15; 422/44–46; 210/739, 742, 767, 85, 90, 94

(56) References Cited

U.S. PATENT DOCUMENTS

| | | | |
|---|---|---|---|
| 4,894,164 A | 1/1990 | Polaschegg | |
| 5,069,662 A | 12/1991 | Bodden | 604/4 |
| 5,178,603 A | 1/1993 | Prince | 604/6 |
| 5,344,392 A | 9/1994 | Senninger et al. | 604/4 |
| 5,411,479 A | 5/1995 | Bodden | |
| 5,423,738 A | 6/1995 | Robinson et al. | 604/4 |
| 5,674,190 A | * 10/1997 | Kelly | 604/6.13 |
| 5,783,093 A | 7/1998 | Holme | 210/767 |
| 5,792,094 A | * 8/1998 | Stevens et al. | 604/4.01 |
| 5,817,045 A | 10/1998 | Sever, Jr. | 604/4 |
| 5,899,873 A | 5/1999 | Jones et al. | 604/4 |
| 5,906,588 A | 5/1999 | Safar et al. | 604/64 |
| 6,336,910 B1 | 1/2002 | Ohta et al. | |

FOREIGN PATENT DOCUMENTS

| | | |
|---|---|---|
| EP | 02657951 | 10/1986 |
| EP | 0649665 | 4/1995 |
| EP | 0803280 A2 | 10/1997 |
| JP | 64027563 | 1/1989 |
| JP | 01259871 | 10/1989 |
| JP | 02041172 | 2/1990 |
| JP | 05168703 | 7/1993 |
| JP | 8266619 | 10/1996 |
| JP | 9290020 | 9/1997 |
| JP | 9290021 | 9/1997 |
| WO | WO8303356 | 10/1983 |
| WO | WO9524940 | 9/1995 |

OTHER PUBLICATIONS

Profound Hypotension with Differential Cooling of the Brain in Dogs, J. Neurosurgery, vol. 24, p. 993–1001, (1966).
Selective Cooling of Brain Using Profound Hemodilution in Dogs, Neurosurgery, vol.. 31, No. 6, p. 1049–1054 (12/92).
Selective Hypothermic Perfusion in Canine Brain, J. Neurosurgery, vol. 38, No 6, Jun. 1996, pp. 1211–1215.
Zukai:Dennetsu–Kogaku no Manabikata (Translated Abstract provided)(Illustration: How to learn heat transfer ngineering) (1$^{st}$ ed. by N. Kitayama, published by Ohmsha (Tokyo) Jul. 20, 1989, pp 104–109).

* cited by examiner

*Primary Examiner*—Angela D. Sykes
*Assistant Examiner*—Leslie Deak

(57) ABSTRACT

There is provided an apparatus which reduces a bleeding amount upon an operation.

A bloodless treating apparatus used upon a surgical treatment of an objet comprises:

(A) a fluid replacement supply unit which quantitatively supplies a fluid replacement into a blood vessel leading to the object (24); and (B) a fluid replacement withdrawing unit which quantitatively withdraws the fluid replacement having passed through the object (24) from a blood vessel coming from the object.

9 Claims, 5 Drawing Sheets

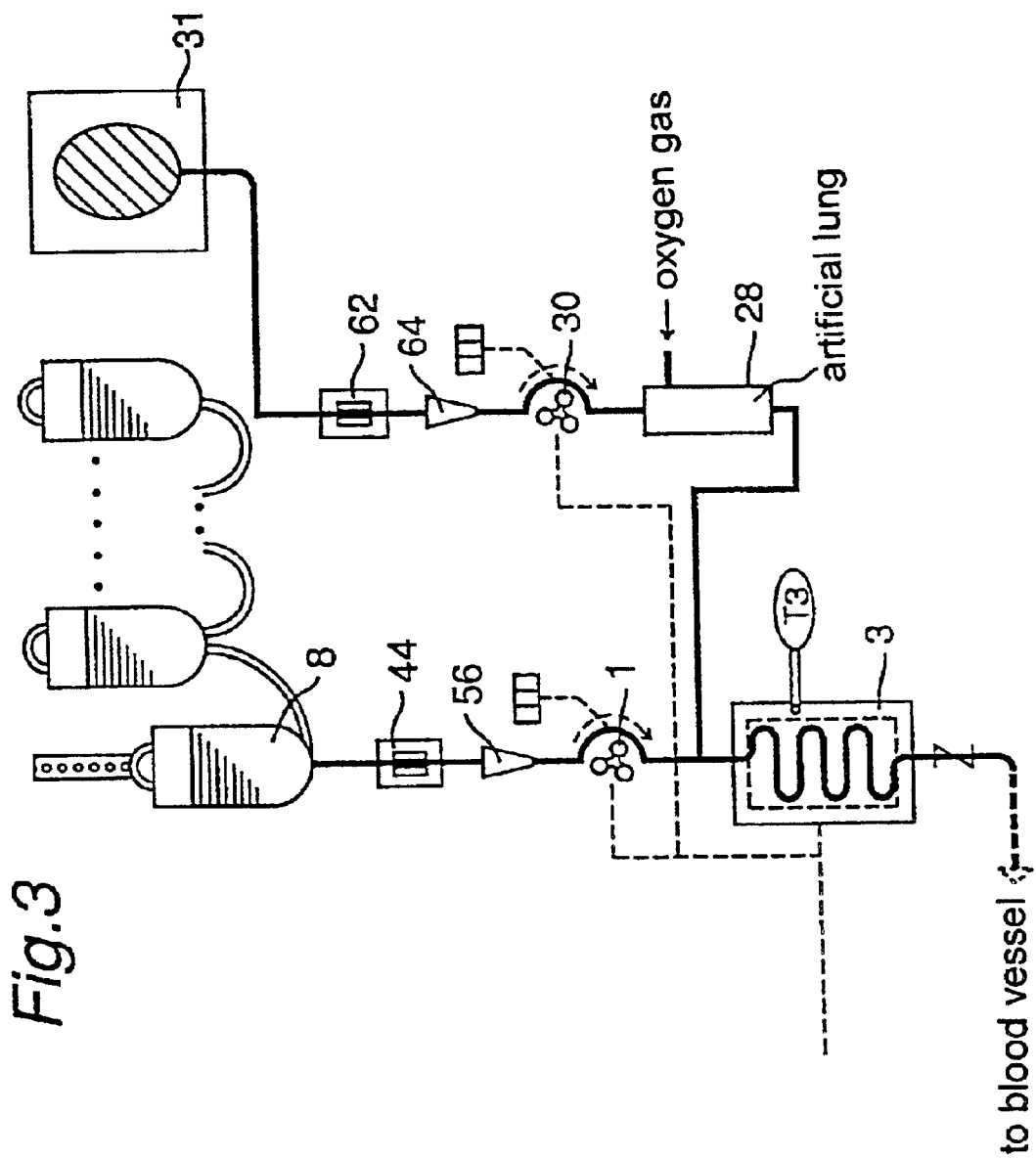

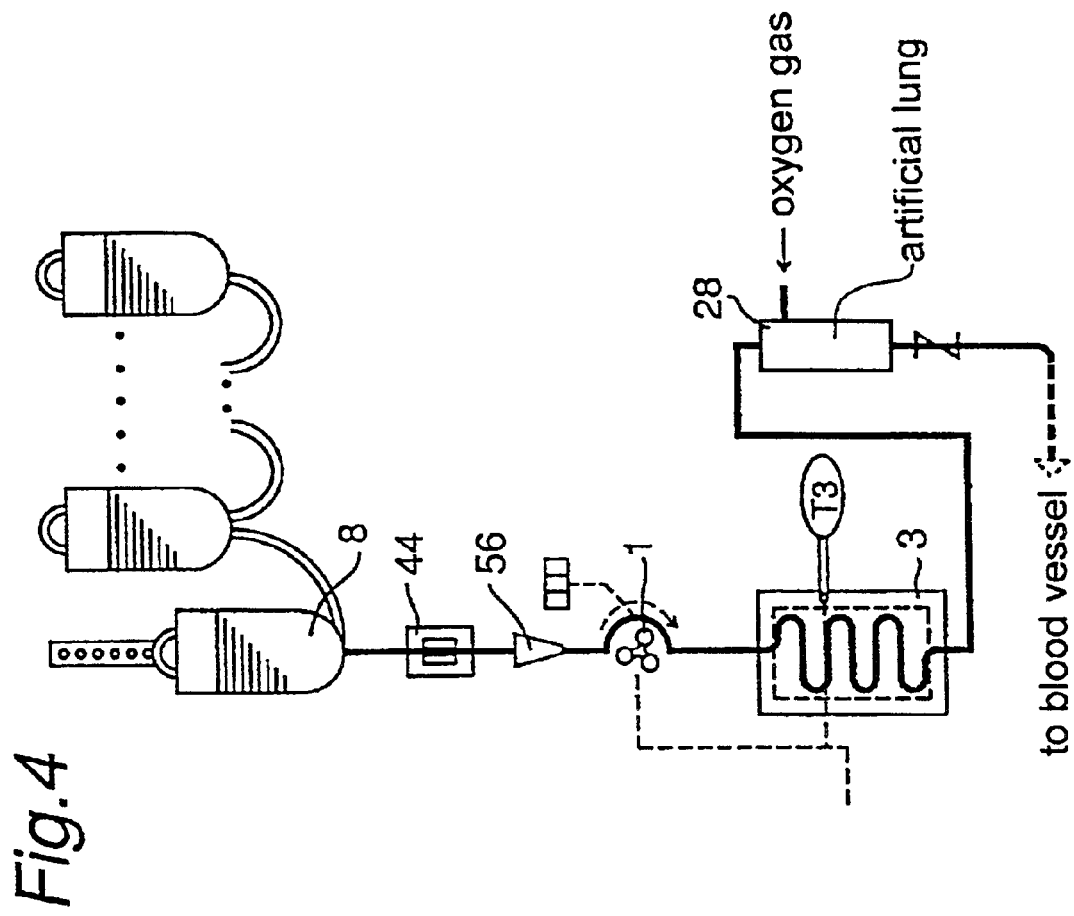

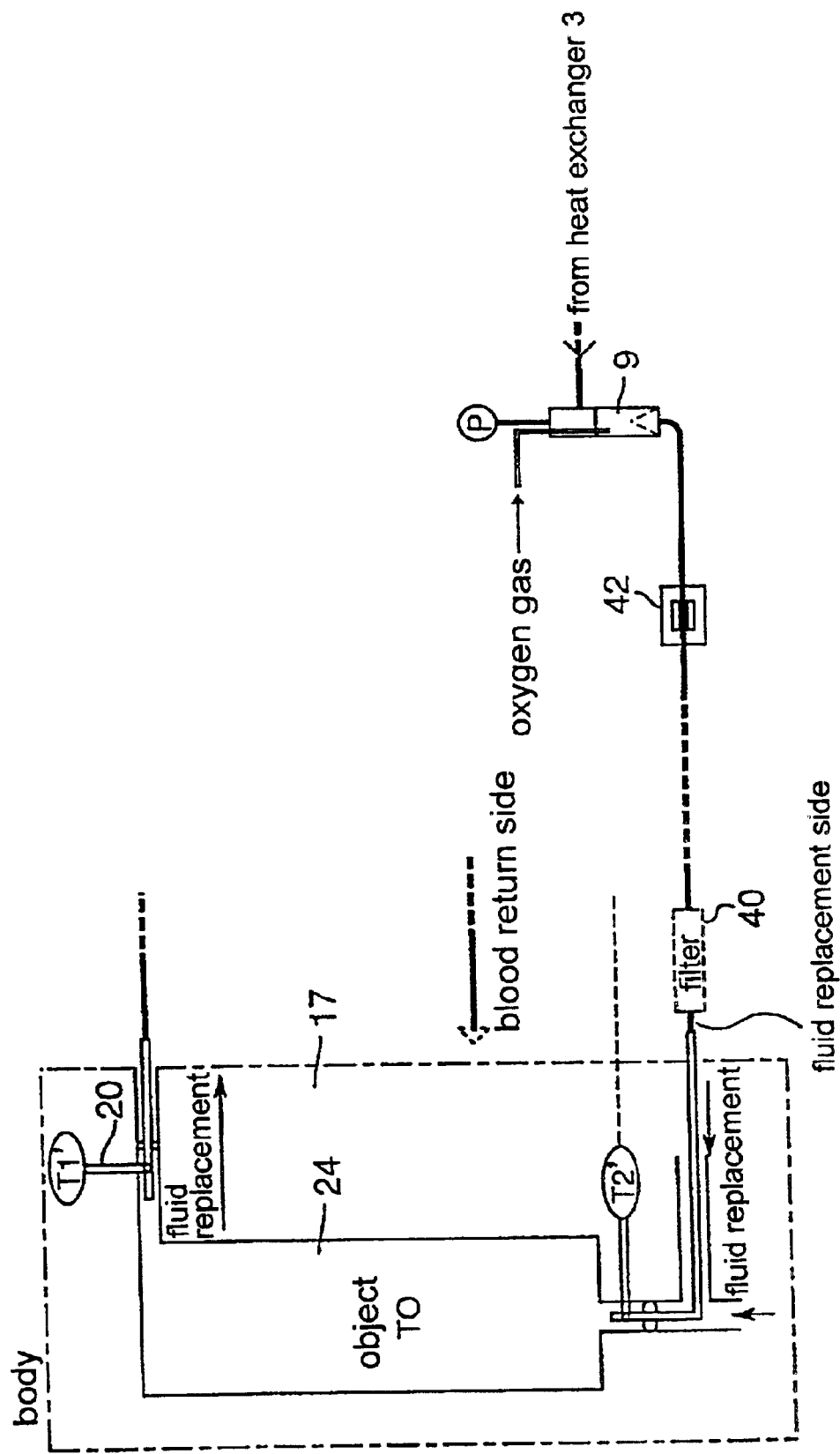

BLOODLESS TREATING DEVICE

This application is a 35 U.S.C. 371 National State filing of PCT/JP00/00696, now published as WO00/47251.

TECHNICAL FIELD

The present invention relates to an apparatus for minimizing a bleeding amount which apparatus is used upon applying a surgical treatment to an object such as an organ, for example an operation, a treatment using an artificial lung or the like in the medical field related to a mammal and especially a human. Hereinafter, such apparatus is also referred to as a "bloodless treating apparatus".

BACKGROUND ART

A surgical treatment such as an operation is applied to an object as a part of a body for various purposes. Upon applying such a surgical treatment, it is of course desirable to reduce a bleeding amount as small as possible, but the bleeding can not be avoided. For example, in the case in which a bleeding amount is large, transfusion with an autologous blood or other's blood is necessary. The large bleeding amount results in a problem of a viewing field in that the object to which the surgical treatment is applied is blinded due to the bleeding blood, and such problem may leads to a failure of the treatment. Additionally, a blood pressure of a patient may be lowered due to the large bleeding amount so that there is a possibility that the treatment itself can not be continued.

In order to solve such problems involved in bleeding, there have been made various attempts for reducing the bleeding amount. For example, it is carried out that the bleeding is suppressed by reducing an incision area and temporarily stop a proximal artery. Further, it is also carried our that bleeding blood is recovered and clarified, followed by returning to the body.

In spite of the above, a bleeding amount is actually large, and blood transfusion is often carried out. Upon the blood transfusion, there is problems related to infectious disease such as AIDS (i.e. acquired immunodeficiency syndrome), hepatitis and so on, and thus from such viewpoint, it is desirable to minimize the bleeding amount. The above blood recovery requires an expensive disposable device and an expensive apparatus, so that it cannot be applied to any surgical treatment.

DISCLOSURE OF INVENTION

Therefore, it is desired to provide an apparatus for reducing an amount of a transfusion blood and preferably avoiding a necessity of the transfusion, by reducing a bleeding amount on an occasion of a surgical treatment such as an operation, as well as for preventing bleeding during the treatment from obstructing a viewing field, so that the treatment is facilitated and the surgical treatment can be made effectively.

The inventors have studied in various ways for solving the problems described above, and finally found that such problems can be solved by supplying a fluid replacement exclusively to an object such as a brain as much as possible.

Thus, the present invention provides a bloodless treating apparatus used on an occasion of a surgical treatment of an objet, which apparatus comprises:

(A) a fluid replacement supply unit which quantitatively supplies a fluid replacement into a blood vessel (afferently) leading to the object; and (B) a fluid replacement withdrawing unit which quantitatively withdraws the fluid replacement from a blood vessel (efferently) coming from the object, the fluid replacement having passed through the object.

In the present invention, the "surgical treatment" is of a broad concept including any treatment, remedy, or examination which involves an injury of a part of a body. The "surgical treatment" includes, for example, an operation, a treatment using an artificial lung and the like. Such treatment includes an incision operation using a knife as well as an operation using an endoscope. The "object" means a part of the body (e.g. extremities, a face, a head, an organ such as a brain, a liver or the like, or a part thereof) which is an object to which the surgical treatment is applied, and the "object" is for example an organ to be operated (e.g. an organ containing cancer cells).

In addition, the "blood vessel leading to the object" means a blood vessel located on an artery side regarding to the object (i.e. a blood vessel through which blood flows into the object), and such blood vessel is one to which the fluid replacement can be supplied (or injected) with an available medical technique. The blood vessel can be any blood vessel as far as it leads to the object. Although the blood vessel may also leads to other portion of the body than the object, such other portion is preferably minimized with an acceptable extent so as to avoid supplying the fluid replacement to such other portion than the object as less as possible. A position of such blood vessel at which the fluid replacement is injected can be any position as far as the supplied fluid replacement is possible to flow into the object, but it is preferable that the position is as close to the object as possible on the blood vessel as described above. It is more preferable that such blood vessel leads into only the object.

The blood vessel generally branches off. If it is not possible to access the blood vessel leading to only the object so as to supply the fluid replacement to the blood vessel because of a restriction as to a location of the object, a thickness of the blood vessel or the like, the fluid replacement can not help being supplied to the blood vessel upstream of a branching off position in some cases. In such cases, although the supplied fluid replacement flows into other portion(s) than a portion as the object by way of the branching out blood vessel(s), injecting "the fluid replacement into a blood vessel leading to the object" in the apparatus of the present invention includes a case in which the fluid replacement is supplied to the branching off blood vessel(s) as far as such case provides substantially no adverse effect upon applying the surgical treatment to the objet using the apparatus of the present invention, that is, as far as other negative effect does not occur relatively to a positive effect provided by using the apparatus of the present invention, and in other words if an advantageous effect is expected as a whole when deducting the negative effect from the positive effect.

On the other hand, the "blood vessel coming from the object" means a blood vessel located on a vein side regarding to the object (i.e. a blood vessel through which blood flows toward the heart from the object), and such blood vessel is one from which the fluid replacement can be withdrawn (or discharged) with an available medical technique. A position of such blood vessel at which the fluid replacement is withdrawn can be any position of such blood vessel, but it is preferable that the position is as close to the object as possible. It is preferable that such blood vessel comes from only the object. Branching off blood vessels are generally join each other at the vein side. If it is not able to access the blood vessel coming from only the object upstream of the joining position so as to withdraw the fluid replacement from the blood vessel because of a restriction as to location of the object, a thickness of the blood vessel or the like, blood derived from the joining blood vessel(s) as described above can not help being withdrawn together with the fluid replacement which has passed through the object in some cases.

In such cases, although the blood flowing from other portions than the object is also withdrawn in addition to the fluid replacement having passed through the object, withdrawing "the fluid replacement from a blood vessel coming from the object, the fluid replacement having passed through the object" in present invention includes a case in which the blood is also withdrawn from thus branding off blood vessel(s) as far as such case provides substantially no adverse effect upon applying the surgical treatment to the objet using the apparatus of the present invention, that is, as far as other negative effect does not occur relatively to a positive effect that the surgical treatment can be advantageously applied, and in other words if an advantageous effect is expected as a whole when deducting the negative effect from the positive effect. In other cases, all of the supplied fluid replacement does not always flow into the object as described above, and it is preferable in such case to additionally withdraw the fluid replacement which has not passed through the object. Thus, in the apparatus of the present invention, withdrawing of the fluid replacement includes a case in which the blood and/or the fluid replacement which has not passed through the object is withdrawn in addition to the fluid replacement which has passed through the object. It is also possible that blood (for example, blood existing in the object prior to the supply of the fluid replacement) is discharged from the portion as the object, and the fluid replacement having passed through the object contains the blood in this case.

In the present invention, "quantitatively supply" means supplying the fluid replacement to the blood vessel in a predetermined amount or with a predetermined flow rate, and "quantitatively withdraw" means withdrawing the fluid replacement from the blood vessel in a predetermined amount or with a predetermined flow rate. It is noted that the predetermined flow rate is not necessarily a constant rate, and includes a case in which the flow rate is varied as predetermined during the supplying or the withdrawing.

As the fluid replacement, any liquid can be used as far as it provides no adverse effect for the surgical treatment and the object. The fluid replacement may includes a component providing a favorable influence for the object and/or the surgical treatment. The fluid replacement, for example, generally contains water as a main component and may further contain an electrolyte, a nutrient, a stabilizer and the like. A particularly preferred fluid replacement is stable at 20 to 50° C. For example, a Ringer's solution, a lactated Ringer's solution, a Ringer's solution containing a low molecular dextrin (for example containing it at 5%), particularly an L-typed one thereof or the like is preferably used as the fluid replacement.

It is noted that when the fluid replacement contains various components, at least a part of the components contained in the fluid replacement can be administered to the object while the fluid replacement passes through the object. Furthermore, the fluid replacement receives various components from the object while it passes through the object. Therefore, kinds and amounts of the components contained in the fluid replacement are generally different between before and after the fluid replacement passes through the object though the main component of the fluid replacement is the water, and the fluid replacement often contains the blood after passing through the object as described above.

When an amount of the blood contained in the fluid replacement which is withdrawn by means of the apparatus of the present invention is small, the withdrawn fluid replacement can be disposed or wasted as it is, and an autologous blood or a transfusion blood can be supplied to the body in an amount corresponding to that of the wasted blood depending on a case. However, when the amount of the blood contained in the fluid replacement is large, it is preferable to recover the blood by removing the water from the withdrawn fluid replacement and return the recovered blood to the body. This recovery of the blood can be carried out by, for example, filtration or dialysis (including diafiltration). Thereby, a loss of the blood can be minimized even if the withdrawn fluid replacement contains the blood.

Accordingly, the apparatus of the present invention in one embodiment preferably comprises:

(C) a blood supply unit which recovers the blood contained in the withdrawn fluid replacement by removing the water from the withdrawn fluid replacement and supplies the recovered blood into other blood vessel to be to the body preferably after controlling a temperature of the recovered blood. In such embodiment, the "other blood vessel" refer to a blood vessel which is different from the blood vessel to be supplied with the fluid replacement, and may be the same as the blood vessel from which the fluid replacement is withdrawn as far as a position to which the recovered blood is supplied locates on somewhere being closer to the heart than the withdrawing position. It is preferable that the "other blood vessel" is a vein.

In the case in which the object is injured to bleed in a considerable amount when the surgical treatment is applied to the object upon an ordinary operation (without using the apparatus of the present invention), when the apparatus of the present invention is used, the fluid replacement is supplied to the object and the fluid replacement existing in the object is mainly discharged whether or not the blood is recovered which is contained in the fluid replacement, so that the bleeding amount is substantially reduced. That is, even in the case of injuring the object, the fluid replacement flows out in place of the blood so that the bleeding amount is substantially reduced when the apparatus of the present invention is used, and thereby the problems involved in the bleeding as described above can be avoided or alleviated.

It is noted that the term of "bloodless" which is used in the present invention does not mean completely no bleeding but means a substantially less bleeding amount upon applying the surgical treatment to the objet by means of the apparatus of the present invention compared with the conventional surgical treatment, thereby the problems in the prior art as described above are substantially avoided or substantially alleviated. Of course, the substantial amount of the bleeding is minimized in the most preferred embodiment.

BRIEF DESCRIPTION OF DRAWINGS

FIG. 3 is a schematic drawing of the apparatus shown in FIG. 1 or 2 which further comprises an artificial lung for oxygenating autologous blood or transfusion blood (only a part of the lung being shown);

FIG. 4 is a schematic drawing of the apparatus shown in FIG. 1 or 2 which further comprises an artificial lung for oxygenating fluid replacement (only a part of the lung being shown); and FIG. 5 is a schematic drawing of the apparatus shown in FIG. 1 or 2 which comprises in place of an artificial lung, a drip chamber for bubbling oxygen gas.

Figure 1:
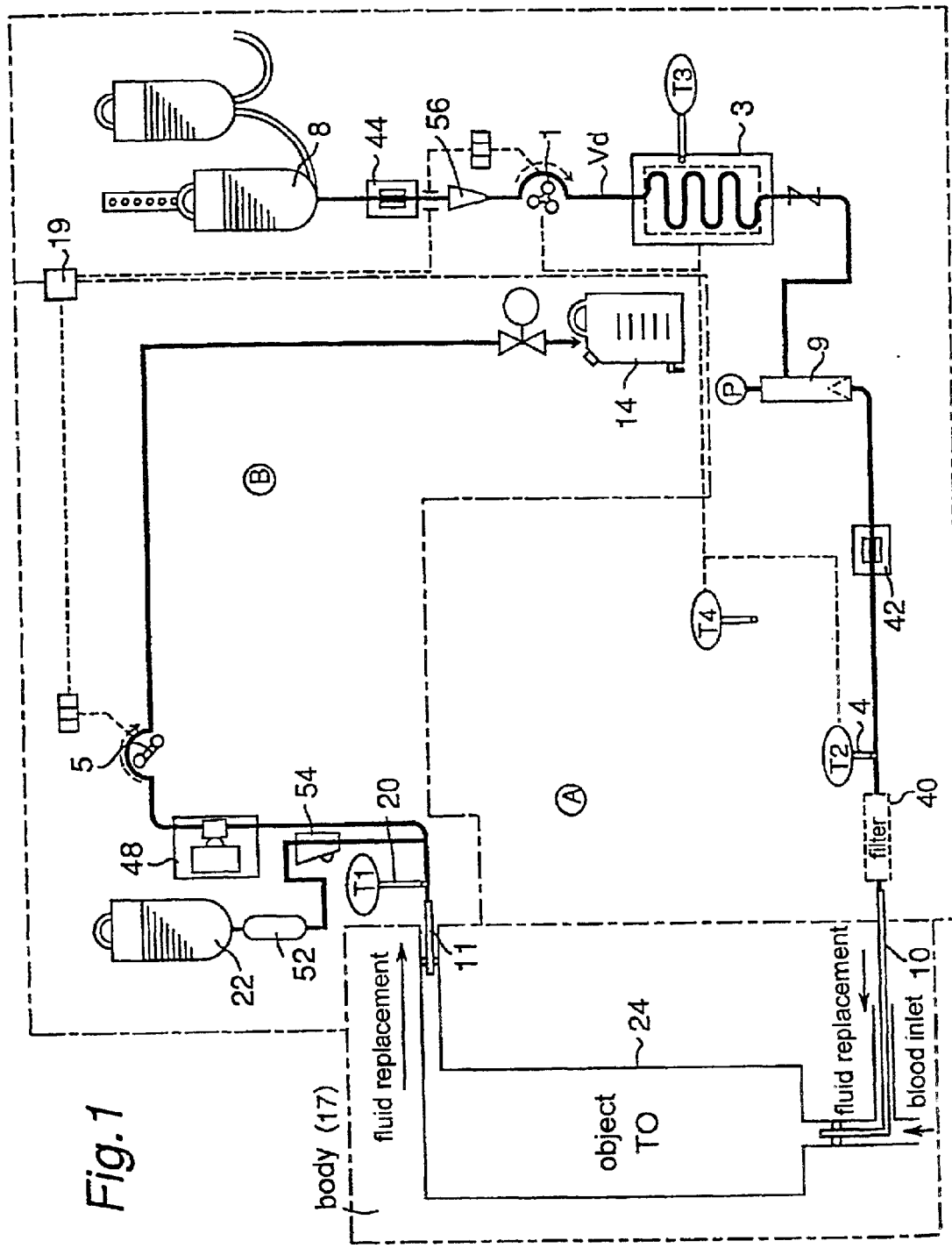
FIG. 1 is a schematic drawing which shows the bloodless treating apparatus in one embodiment of the present invention.

It is noted that numerals in the drawings denote the following elements:

| | |
|---|---|
| 1 | fluid replacement supply pump, |
| 3 | heat exchanger, |
| 4 | supplied fluid replacement temperature sensor, |
| 5 | fluid replacement withdrawal pump, |
| 6 | heat exchanger, |
| 7 | water removal pump, |
| 8 | fluid replacement container, |
| 9 | drip chamber, |
| 10, 11 | catheter, |
| 12 | drip chamber, |
| 13 | blood recovery element, |
| 14 | removed water tank, |
| 15 | catheter, |
| 16 | drip chamber, |
| 17 | body, |
| 18 | heparin supplier, |
| 19 | supply/removal controlling mechanism, |
| 20 | withdrawn fluid replacement temperature sensor, |
| 22 | fluid replacement bottle, |
| 24 | object, |
| 28 | artificial lung, |
| 30 | pump, |
| 31 | transfusion blood (or autologous blood), |
| 40 | filter, |
| 42 | bubble detector, |
| 44 | fluid empty detector, |
| 46 | bubble detector, |
| 48 | pressure measurement element, |
| 50 | temperature sensor, |
| 52 | drip chamber, |
| 54 | clamp, |
| 58 | drip chamber, |
| 62 | fluid empty detector, |
| 64 | drip chamber, |
| 70 | protamine pump. |

DETAILED DESCRIPTION OF THE INVENTION

It is preferable to apply the surgical treatment at a predetermined temperature in view of maintaining the condition of the object in many cases. In some cases, it is preferable to maintain the object at a low temperature in order, for example, to maintain the objet at a condition of a low blood pressure, present a swelling of the object, or inhibit a metabolism of the object. In other cases, it is preferable to maintain the object at a high temperature in order to kill cancer cells existing in the object or recover the temperature of the object.

More concretely, regarding to the surgical treatment with a temporary stopping of a bloodstream by means of clipping of a cerebral aneurysm, it is preferable to maintain the temperature of the brain as the object at a low temperature of about 16° C. Regarding to a combined treatment of a cancer therapy with a chemotherapy and/or a radiotherapy, it is preferable to maintain the temperature of the cancer tissues as the object at a high temperature of about 43° C. It is noted that the low temperature or the high temperature refers to a temperature on the basis of the body temperature.

Accordingly, there is provided an apparatus for minimizing the bleeding amount while controlling the temperature of the object at a predetermined temperature in other embodiment of the present invention. Such apparatus can controls a temperature of the object to which the surgical treatment is applied by measuring a temperature of the fluid replacement withdrawn from the blood vessel and controlling (or adjusting) a temperature of the fluid replacement to be supplied to the blood vessel based on thus measured temperature.

That is, when it is intended to control the temperature of the object at a predetermined temperature depending on the surgical treatment to be applied to the object, the temperature of the object is more precisely controlled by controlling (or adjusting) the temperature of the fluid replacement which is to be supplied, whereby the surgical treatment can be carried out more effectively. It is noted that such temperature controlling will be explained hereinafter with reference to a case of mainly cooling the object to a predetermined temperature as an example. Since a case of warming the object is not substantially different from the case of cooling the object except warming of the object, those skilled in the art will readily carry out the case of warming the object based on the example in which the object is cooled.

It is noted that depending on the kind of the surgical treatment, the kind of the object to which the surgical treatment is applied and the like, a temperature at which the object is to be kept (for example, a temperature to which the object is to be warmed, or a temperature to which the object is to be cooled), namely the predetermined temperature of the object is determined when applying the surgical treatment to the objet while controlling the temperature of the object using the apparatus of the present invention. Therefore, the predetermined temperature at which the object is to be maintained using the bloodless treating apparatus according to the present invention as well as an accuracy of such temperature maintenance is properly selected by for example a doctor depending on the treatment to be applied to the object.

Then, the present invention provides, in one embodiment, a bloodless treating apparatus used for the surgical treatment while keeping (or shifting (or changing) from an original temperature before the surgical treatment or the use of the apparatus and then keeping) a temperature of an object which is a part of a body at a predetermined temperature (T0), which apparatus comprises:

(A) a fluid replacement supply unit which quantitatively supplies (or meters) a fluid replacement into a blood vessel leading to the object; and (B) a fluid replacement withdrawing unit which quantitatively withdraws the fluid replacement having passed through the object, from a blood vessel coming from the object; and (C) optionally a blood supply unit which recovers blood existing in the fluid replacement which has been withdrawn, and returns the blood into other blood vessel preferably after controlling a temperature of the recovered blood, the fluid replacement withdrawing unit comprising a withdrawn fluid replacement temperature sensor which measures a temperature of the withdrawn fluid replacement, and the fluid replacement supply unit comprising a means which controls (or adjusts) the temperature of the fluid replacement to be supplied (injected) based on a different extent between the measured withdrawn fluid replacement temperature (T1) and the predetermined temperature of the object (T0) (such as a difference $\Delta T$ ($=T1-T0$), a ratio TR (=T1/T0) or the like). It is noted that the means which controls the temperature of the fluid replacement to be supplied serves to make the different extent smaller (or to make the ratio closer to 1 in the case of the ratio). By means of the apparatus as described above, it is possible to carry out the more accurate control wherein the object to which the surgical treatment is applied is kept at a temperature which is close to the predetermined temperature, and preferably substantially at the predetermined temperature.

In the apparatus in the aforementioned embodiment of the present invention, the fluid replacement which is to be withdrawn out preferably passes through the object to which the surgical treatment is applied, and the fluid replacement is discharged as soon as possible after passing through the object, and therefore it is assumed that the temperature of the withdrawn fluid replacement measured by the withdrawn fluid replacement sensor (T1) represents the temperature of the object to which the surgical treatment is applied. The term "represent(s)" herein is intended to mean that the temperature of the withdrawn fluid replacement (T1) is not necessarily the temperature of the object itself (although it is preferably the temperature of the object itself), variation of the fluid replacement temperature (T1) or the fluid replacement temperature (T1) being relatively higher or lower corresponds to variation of the object temperature or the object temperature being higher or lower. Particularly, when the predetermined temperature at which the object is to be maintained or the accuracy of the temperature maintenance at the predetermined temperature is not so strict, for example, the above assumption is applicable. Particularly, when a supply rate of the fluid replacement is large depending on the treatment which is applied to the object so that a withdrawal rate of the fluid replacement is large, a temperature change of the withdrawn fluid replacement during a period in which it is moved from the object to the withdrawn fluid replacement temperature sensor, and in particular the temperature change due to the body temperature may be neglected since the period required for the withdrawn fluid replacement to flow from the object to the outside of the body after it is supplied to the object becomes short. In such case, it is often that the temperature of the withdrawn fluid replacement (T1) is regarded as a true temperature of the object at that time which is to be kept at the predetermined temperature (T0).

In the apparatus described above, the "means which controls a temperature of the fluid replacement to be supplied based on a different extent between the measured withdrawn fluid replacement temperature (T1) and the predetermined temperature of the object (T0)" is a means which obtains the different extent (such as a difference or a ratio) between the measured withdrawn fluid replacement temperature and the predetermined temperature of the object, and increases or decreases the temperature of the fluid replacement to be supplied based on the different extent. It is noted that when there is substantially no different extent, the means keeps the temperature of the fluid replacement as it is.

Concretely, when the withdrawn fluid replacement temperature (T1) is higher than the predetermined temperature of the object (T0) (that is, when T1−T0>0 or T1/T0>1), the above means functions to decrease the temperature of the fluid replacement to be supplied (or injected). Such function can be achieved by forming a control system which senses the different extent between the withdrawn fluid replacement temperature (T1) and the predetermined temperature of the object (T0) and warms and/or cools the fluid replacement to be supplied into the object based on the different extent so as to make the different extent smaller (or to make the ratio closer to 1 in the case of the ratio). The formation of such system is well known in the field of the temperature control. For example, a manner can be employed in which a set temperature of a heat exchanger (or a warming/cooing device) which controls the temperature of the fluid replacement supplied into the object is changed (that is, the temperature of the fluid replacement to be supplied is lowered) depending on the sensed different extent. Also, when the withdrawn fluid replacement temperature (T1) is lower than the predetermined temperature of the object (T0) (that is, when T1−T0<0 or T1/T0<1), the above means functions to increase the temperature of the fluid replacement to be supplied.

It is noted that when there is substantially no different extent (that is, when T1−T0=0 or T/T0=1, and thus for example when the temperature control of the object seems to be working satisfactorily), the above means functions to keep the temperature of the fluid replacement to be supplied at that time.

In a case where the temperature of the fluid replacement may change after the fluid replacement has arrived at the object and has once reached a temperature which is the same as or near the temperature of the object in the object and until the fluid replacement arrives at the withdrawn fluid replacement temperature sensor, the above explanations are not applicable. Also, in a case where the fluid replacement is withdrawn without its temperature having been thermally equilibrium with the object because of a short residence time of the fluid replacement in the object since a supply rate of the fluid replacement is too large (especially at the beginning of the fluid replacement supply), the above explanations are not applicable, If there is no change in T1 when the supply rate of the fluid replacement is temporarily increased and/or decreased a little, the above explanations will be applicable. In general, it is preferable to follow the supply rate which is described concretely in the explanations as below.

Alternatively, when the supply rate of the fluid replacement into the inside of the body may be changed depending on the treatment for the object, it is also possible to use a means which changes the supply rate of the fluid replacement into the inside of the body in place of or in addition to the above means which adjusts the temperature of the fluid replacement. That is, it is utilized that an amount of heat transferred from the fluid replacement to the object or from the object to the fluid replacement changes when the supply rate of the fluid replacement is changed. Generally, when the supply rate is increased, an amount of heat transferred is increased. That is, when the temperature of the fluid replacement is lower than that of the object, the object is further cooled by the increase of the supply rate of the fluid replacement. Also, when the temperature of the fluid replacement is higher than that of the object, the object is further warmed by the increase of the supply rate of the fluid replacement, and when the supply rate of the fluid replacement is decreased, reversed phenomena are observed. This embodiment to change the supply rate is particularly preferably used for changing the temperature of the object a little.

In other embodiment, the bloodless treating apparatus according to the present invention comprises a supplied fluid replacement temperature sensor in addition to the withdrawn fluid replacement temperature sensor, and the former sensor measures a temperature of the fluid replacement which is supplied to object (a supplied fluid replacement temperature, T2). In this embodiment, an averaged value. (Tav, an averaged temperature such as an arithmetical mean, a logarithmic mean, a weighted mean or the like) of the supplied fluid replacement temperature (T2) and the withdrawn fluid replacement temperature (T1) is assumed to be represent the temperature of the object to which the surgical treatment is applied in place of the withdrawn fluid replacement temperature (T1) in the apparatus in the aforementioned embodiment of the apparatus of the present invention, and a different extent between the averaged temperature (Tav) and the predetermined temperature of the object (T0) is taken into consideration in place of the different extent between the withdrawn fluid replacement temperature and the predetermined temperature of the object in the aforementioned embodiment. The temperature of the fluid replacement to be supplied is controlled so that such former extent becomes smaller (or as to the ratio, it becomes closer to 1 in the case of the ratio). The other features are substantially the same as those of the apparatus of the aforementioned embodiment.

Thus, in the apparatus of this embodiment, the "means which controls a temperature of the fluid replacement to be supplied based on a different extent between the withdrawn fluid replacement temperature (T1) and the predetermined temperature of the object (T0)" is a means which obtains the different extent between the predetermined temperature of the object and the averaged temperature of the withdrawn fluid replacement temperature and the supplied fluid replacement temperature, and increases or decreases, or keeps the temperature of the fluid replacement to be supplied based on thus obtained different extent. That is, the different extent between the predetermined temperature and the withdrawn fluid replacement temperature is considered while further considering the supplied fluid replacement temperature. Similarly to the apparatus of the aforementioned embodiment, the supply rate change of the fluid replacement may be applied in place of or in addition to the control of the fluid replacement temperature.

Concretely, when the averaged temperature (Tav) is higher than the predetermined temperature of the object (T0) (that is, when Tav−T0>0 or Tav/T0>1), the above means functions to decrease the temperature of the fluid replacement to be supplied. When the averaged temperature (Tav) is lower than the predetermined temperature of the object (T0) (that is, when Tav−T0<0 or Tav/T0<1, and for example when cooling by means of the fluid replacement seems to be excessive), the above means functions to increase the temperature of the fluid replacement to be supplied. It is noted that when there is substantially no different extent (that is, when Tav−T0=0 or Tav/T0=1, and thus for example when the temperature control of the object seems to be working satisfactorily), the above means functions to keep the temperature of the fluid replacement to be supplied at that time. Similarly to the apparatus of the aforementioned embodiment, the formation of a control system which obtains the averaged temperature (Tav) of the supplied fluid replacement temperature (T2) and the withdrawn fluid replacement temperature (T1), obtains the different extent between the averaged temperature (Tav) and the predetermined temperature of the object (T0), and controls the temperature and/or the supply rate of the fluid replacement to be supplied based on the different extent is well known to those skilled in the art.

In any embodiment of the present invention as described above, the withdrawn fluid replacement temperature or the averaged temperature of the withdrawn fluid replacement temperature and the supplied fluid replacement temperature is regarded as described above to represent and preferably be equal to the actual temperature of the object to which the surgical treatment is applied, and it is therefore preferable that the supplied fluid replacement and/or the withdrawn fluid replacement are not so thermally affected by others except the object. Thus, it is preferable that the temperatures of the supplied fluid replacement and the withdrawn fluid replacement are measured as closely to the object as possible. Therefore, it is preferable that the withdrawn fluid replacement is measured at a position which is immediately downstream of the outlet of the withdrawn fluid replacement from the blood vessel, and the supplied fluid replacement is measured at a position which is immediately upstream of the inlet of the supplied fluid replacement into the blood vessel.

In any aspect of the present invention, the supply and the withdrawal of the fluid replacement are carried out through catheters as described below. It is more preferable to use a balloon catheter (having a conduit for supplying or discharging a fluid). The use of the balloon catheter is advantageous in that a flow of other fluid in the blood vessel can be stopped by inflating the balloon in the blood vessel, and thereby it is possible to supply substantially only the fluid replacement to the blood vessel leading to the object, and it is also able to withdraw substantially all fluid (which comprises the fluid replacement as a main component) flowing through the blood vessel coming from the object. In a particularly preferable embodiment, a thermister is located at one end of each of the catheters (one for the withdrawal of the fluid replacement and the other for the supply of the fluid replacement) which end is closer to the object (i.e. the distal end or the leading end when the catheter is inserted) or a vicinity of such end. The withdrawn fluid replacement temperature (T1) and/or the supplied fluid replacement temperature (T2) are measured while such catheters are inserted to be located as near the object as possible, whereby the accuracy of the object temperature assumption as described above is further improved so that the accuracy of keeping the object at the predetermined temperature is improved.

In the apparatus of the present invention, when the blood is recovered from the withdrawn fluid replacement, the blood supply unit preferably recovers the blood by removing the water from the withdrawn fluid replacement so as to preferably attain a hematocrit value (of the recovered blood) of at least 70% of that of a usual blood to which no fluid replacement is supplied (usually, a normal hematocrit value of a patient to whom the bloodless treating apparatus is applied), and thereafter controls the temperature of the recovered blood to a temperature around the body temperature if necessary, and returns the blood into the body via other blood vessel than that used for supplying or withdrawing the fluid replacement. Therefore, an amount of the lost blood of the patient by the application of the surgical treatment is minimized.

The surgical treatment which can be carried out by using the apparatus of the present invention is exemplified by an operation (particularly such as a brain tumor resection, a clipping operation of a cerebral aneurysm and the like), a hepatectomy and the like, but not limited thereto. In general, when the object may bleed because of the treatment, the bleeding amount can be reduced by carrying out the treatment while using the apparatus of the present invention.

When the bloodless treatment is carried out by using the apparatus according to the present invention, it is generally preferable to supply the fluid replacement which has been adjusted to the predetermined temperature (T0) beforehand upon starting to use the apparatus. Particularly, when the averaged temperature is used as described above, since the supplied fluid replacement temperature (T2) is measured, it is preferable to control the temperature of the supplied fluid replacement such that T2 becomes the predetermined temperature (T0). Upon such control, it is desirable to take effects of various parameters (or factors, including a room temperature) into the consideration as described below.

In a case where the bloodless treatment is carried out by using the apparatus according to the present invention, it may be not preferable to rapidly change (for example cool or warm) the temperature of the object to the predetermined temperature (T0) when the predetermined temperature is greatly different from the temperature of the object before the supply (usually the body temperature in the normal condition). This is because the rapid temperature change of the object gives a certain shock, and for example electrolyte balance is broken, which may not be preferable. Thus, in such case, a manner is preferably employed in which a provisional predetermined temperature (T0-1) which is near the temperature before the supply and which is between the temperature before the supply and the predetermined temperature is set so that the temperature of the object reaches T0-1 first, then a next provisional predetermined temperature (T0-2) is set by shifting the provisional temperature toward the predetermined temperature a little so that the temperature of the object reaches T0-2, and then an additional next provisional predetermined temperature is set if necessary, and the temperature of the object finally approaches the original predetermined temperature (T0) in steps.

For example, in a case in which the object is to be cooled from 37° C. to 25° C. as the predetermined temperature (T0), the provisional predetermined temperature (T0-1) is first set at 35° C. so that the object temperature reaches 35° C., then the next provisional predetermined temperature (T0-2) is set at 33° C. when the object temperature approaches or reaches 35° C. so that the object temperature reaches 33° C., whereby the object temperature thus approaches 25° C. as the original predetermined temperature (T0) little by little in steps. The manner in which the object temperature approaches the predetermined temperature may be stepwise as described above or continuous. When the object temperature is raised reversely, the above is applicable similarly. When the object is warmed, the similar is applicable. It is of course possible to rapidly cool or warm if no problem occurs when the object temperature is changed to the predetermined temperature rapidly.

When the bloodless treatment is applied to a selected object while the temperature of the object is adjusted to the predetermined temperature (T0) by using the apparatus of the present invention, in one embodiment a temperature of the fluid replacement to be supplied is controlled first by means of a fluid replacement temperature controller such that the temperature of the fluid replacement to be supplied becomes T0 (which may be the provisional temperature as the above). The fluid replacement thus controlled is supplied into the inside of the body.

When only the temperature of the withdrawn fluid replacement temperature (T1) is measured upon the supply of such fluid replacement, the fluid replacement temperature controller which has been set at the predetermined temperature (T0) is re-set based on the measurement of the withdrawn fluid replacement temperature (T1), that is the temperature of the fluid replacement to be supplied in the fluid replacement temperature controller is re-adjusted (namely, the temperature is set higher or lower than T0 or the temperature is kept).

Also, when the supplied fluid replacement temperature (T2) is further measured in addition to the withdrawn fluid replacement temperature (T1), the average temperature of these temperature is obtained, and then the averaged temperature is compared with the predetermined temperature (T0) to obtain the different extent followed by re-controlling the fluid replacement temperature controller again. It is noted that with regard to the predetermined temperature (T0), it may be preferable to set a provisional predetermined temperature, based on which the fluid replacement temperature controller is adjusted followed by gradually shift the provisional predetermined temperature so that the original predetermined temperature is finally reached as described above.

After having made the object temperature reach the predetermined temperature, returning the object temperature to the original object temperature (that is, recovering the object temperature), which temperature is usually the body temperature in a normal condition, truly corresponds to warming or cooling the object to the predetermined temperature. Therefore, the apparatus according to the present invention may be used for a temperature recovering in which a temperature of the object is returned to the original temperature of the object which has been shifted to the predetermined temperature through the application of the bloodless treatment. That is, the control of the object temperature after carrying out the bloodless treatment may be carried out by using the same apparatus.

It is noted in a case in which the object temperature is shifted to the predetermined temperature, and in particular the object is warmed, that it may be preferable to use oxygen containing blood as the fluid replacement when the object needs oxygen for the purpose of its metabolism. That is, it may be preferable that not using for example a Ringer's solution as the fluid replacement, at least a portion and optionally most of the fluid replacement is replaced with blood (autologous blood or transfusion blood) as described below. When the blood is supplied as above, it is preferable that the blood is oxygenated by for example an artificial lung. In this embodiment, warming is applicable to a case in which the object is warmed from its normal body temperature to a higher temperature as well as a case in which the object is returned from its selectively cooled temperature to its original normal body temperature, and cooling is vice versa.

It is noted that the present invention also provides a method for carrying out the bloodless treatment or a method for reducing a bleeding amount upon the surgical treatment applied to the objet. The method comprises the steps of:

(A) quantitatively supplying a fluid replacement, of which temperature has been preferably adjusted, into a blood vessel leading to the object by means of a fluid replacement supply unit; and (B) quantitatively withdrawing the fluid replacement having passed through the object from a blood vessel coming from the object, and (C) optionally recovering blood contained in the fluid replacement which has been withdrawn and returning the blood into a body via other blood vessel preferably after controlling a temperature of the recovered blood. In such case, it is preferable to measure a temperature of the withdrawn fluid replacement, and control a temperature of the fluid replacement which is quantitatively supplied based on a different extent between the measured withdrawn fluid replacement temperature and the predetermined temperature of the object. Alternatively, it is possible to further measure the temperature of the fluid replacement to be quantitatively supplied and control the temperature of the fluid replacement which is quantitatively supplied based on a different extent between the predetermined temperature of the object and an averaged temperature of the quantitatively supplied fluid replacement temperature and the withdrawn fluid replacement temperature in place of the different extent between the withdrawn fluid replacement temperature and the predetermined temperature of the object.

Also, temperature control of the fluid replacement to be quantitatively supplied is preferably carried out while considering heat transfer between the fluid replacement and a surrounding of the apparatus until the fluid replacement is supplied into the blood vessel. In addition, it is preferable that the temperature of the fluid replacement to be quantitatively supplied has been adjusted to the predetermined temperature of the object when starting the above method.

With the apparatus according to the present invention, a leading end of a catheter is located at a certain position, in an artery directly leading to the object to which the surgical treatment is applied, said certain position being the closest to the object with an available medical technique, so as to supply the fluid replacement to the object via the catheter, and a leading end of the catheter is located at a certain position in a vein directly coming from the object, the position being the closest to the object with the available medical technique, so as to withdraw the fluid replacement which has passed through the object via the catheter, and then the withdrawn fluid replacement is disposed or wasted as it is depending on a situation of the withdrawn fluid replacement.

Alternatively, when an amount of the blood contained in the fluid replacement is large, blood which is in a condition similar to the original blood and preferably which is substantially equivalent to the normal blood is recovered by removing water from the withdrawn fluid replacement, and the recovered blood is returned into a body through a catheter and at a position of other blood vessel such as a vein which position is closer to the heart (so-called a heart side position) and which vein directly or indirectly comes from the above-mentioned vein from which the fluid replacement is withdrawn after a temperature of the recovered blood is adjusted (for example returned to the body temperature), so that the surgical treatment can be safely applied to the object without changing and preferably without substantially increasing an amount of body fluid which is kept in the body and without greatly reducing an amount of the blood in the body.

Using the apparatus according to the present invention, for example when a surgical treatment such as a clipping operation of an aneurysm at a distal end of a basilar artery as the object, a balloon catheter is inserted along a femoral artery to locate its leading end at a distal portion of an origin part of a vertebral artery and the fluid replacement is supplied to a cerebellum and a brain stem, and on the other hand, another balloon catheter is inserted along a femoral vein to locate its leading end in an internal jugular vein and the fluid replacement which has passed through the object is withdrawn. When the blood is recovered from the withdrawn fluid replacement, the recovered blood is returned into the body through the femoral vein.

Further, for example when the surgical treatment such as excision (or resection) is applied to a hepatocellular carcinoma as the object, a balloon catheter is inserted along a femoral artery to locate its leading end at a distal portion of an origin part of a hepatic artery and the fluid replacement is supplied to the tumor portion, and on the other hand, another balloon catheter is inserted along a femoral vein to locate its leading end in a hepatic vein and the fluid replacement which has passed through the object is withdrawn. When the blood is recovered from the withdrawn fluid replacement, the recovered blood is returned into the body through the femoral vein.

Generally, the fluid replacement is injected into an artery belonging to the object to which the surgical treatment is applied at a position of the artery which is as closer to the object as possible with the available medical technique, and the fluid replacement is withdrawn from a vein belonging to the object at a position which is as closer to the object as possible with the available medical technique. A portion at which the recovered blood is returned is not particularly limited.

In one case, the vein from which the fluid replacement is withdrawn is preferably a vain which is intimately related to the artery belonging to the object (thus, a vain in which much and preferably most of the blood having passed through such artery gathers). A portion at which the recovered blood is returned is not particularly limited and may be in a vein in general, and when such vein is the same as the vain from which the fluid replacement is withdrawn, the blood is returned at a position closer to the heart. In order to make a temperature change of the fluid replacement small after the temperature of the fluid replacement reaches that of the object, the fluid replacement is preferably withdrawn at a position which is as closer to the object as possible as to the vain.

When the surgical treatment is carried out while using the apparatus according to the present invention, it is possible to avoid extreme overhydration of the patient by keeping amounts of the supplied fluid replacement and the withdrawn fluid replacement almost not different and preferably keeping them substantially the same (thus equal). The amounts being almost not different does not necessarily mean that flow rates are equal, and there is no problem in general as far as the total amounts are equal while avoiding an unacceptable overhydration. Therefore, for example, a flow rate of the supply (i.e. supply rate) may be of a finite value, and a flow rate of the withdrawal (i.e. withdrawal rate) may be zero at an initial stage of a surgical treatment, both of the flow rates may be substantially equal at an intermediate stage, and the flow rate of the supply may be zero and the flow rate of the withdrawal may be of a finite value at a final stage of the surgical treatment. If the withdrawn fluid replacement contains blood which is not derived from other(s) except the object, such blood is not taken into account in the above quantitative relationship.

Adjustment of the quantitative relationship as described above may be varied depending on a condition of the patient, a kind of the surgical treatment and the like.

When the fluid replacement is needed to temporarily stay at the object for a long time, the supply amount of the fluid replacement can be made large compared with the withdrawal amount of the fluid replacement, and only the object may be overhydrated temporarily if it is acceptable.

In the apparatus according to the present invention, when the blood is recovered by means of the fluid replacement supply unit, the blood temperature is adjusted before it is returned to the body inside, and such adjustment is preferably carried out by heat exchange, and particularly by indirect heat exchange. An apparatus having a heater and/or a cooler for the heat exchange is not particularly limited. In any case, it is possible that the predetermined temperature of the recovered blood is achieved by immersing a conduit through which the recovered blood flows in a constant-temperature bath set at a predetermined temperature (which is usually around the body temperature), and such heat exchanging manner is preferable. In one embodiment, when it has been known beforehand that only warming or cooling is carried out, the heat exchanger may comprise only a heater or a cooler.

The fluid replacement used in the present apparatus is not particularly limited as far as it is possible to be cooled or warmed in an appropriate manner, and it is possible to be supplied into the body through a blood vessel so that the bloodless treatment of the present invention can be carried out. Concretely, an aqueous solution which contains a nutrient and/or an electrolyte may be exemplified as the fluid replacement, and an isotonic solution such as a Ringer's solution, a lactated Ringer's solution, a Ringer's solution containing a low molecular dextrin (for example containing it at 5%) or the like is particularly preferably used as the fluid replacement, but not limited thereto.

In one embodiment, the apparatus according to the present invention comprises a fluid replacement temperature controller as the means to adjust a temperature of the fluid replacement to be supplied. The controller may be the indirect heat exchanger as described above, and for example one may be used in which an appropriate liquid (which is usually water) as a heat transfer medium is charged in a vessel equipped with a heater and/or a cooler and a tube which supplies the fluid replacement is located in the liquid in for example a spiral form. By controlling a temperature of the liquid by using the heater and/or cooler, a temperature of the fluid replacement at an exit of the fluid replacement temperature controller (T3) can be controlled.

It is noted that when a liquid such as the fluid replacement, blood or the like is warmed and/or cooled, the apparatus comprising a heating means (for example, an electric resistive heater) and/or a cooling means (for example, a cooler using a coolant) may be used as described above, and in a preferable embodiment, an warming/cooling apparatus comprising a Peltier element is used. It is noted that warming includes a case in which a temperature is returned to an original temperature after cooling, and that cooling includes a case in which a temperature is returned to an original temperature after warming, both of which may be referred to as temperature recovering (or returning).

The warming/cooling apparatus comprising the Peltier element warms or cools depending on an electric current direction (thus, polarity) across the element, and a thermal dose (or flux) upon warming or cooling depends on an amperage. When the Peltier element is used, switching between warming and cooling may be carried out freely electrically and the amperage may be increased and decreased easily and precisely so that response and sensitivity of the temperature control are good and the temperature control is accurate. The Peltier element has been known for a long time, it has not been known or done that its advantage is very conveniently utilized when the features of the element are employed in the bloodless treating apparatus which may be used for the various treatments in the medical field.

For example, the temperature of the fluid replacement, the blood or the like immediately after leaving the warming and/cooling apparatus is measured, and the measured result is fed back to a controller of the warming and/cooling apparatus, so that increase or decrease of an amount of the electric current through the Peltier element and switching of its polarity may be carried out with a good sensitivity and accuracy. The body condition of a patient to whom the bloodless treating apparatus is used may change momentarily, and when the apparatus according to the present invention is used, such change can be detected through T1. Thus, it is preferable that an extent of warming/cooling of the fluid replacement to be supplied into the body, the blood to be returned to the body or the like is freely changed and switching between warming and cooling is freely carried out, and in order to be thus preferable, the warming/cooling apparatus comprising the Peltier element is preferably used, which is particularly preferable for controlling the temperature recovery.

More particularly, when an electric current is passed across the Peltier element, one junction thereof generates heat to be a higher temperature and the other junction thereof absorbs heat to be a lower temperature, and when the polarity of the voltage applied to the Peltier element is reversed, the temperature relationship between the junctions is reversed. Usually, one junction is warmed or cooled by using air at a room temperature, and for example by blowing air using a fan so that a thermal energy is transferred between the junctions. Usually, thus warmed or cooled junction is contacted with the fluid replacement, the blood or the like indirectly (for example through a plastic film, a metal thin film or the like) for the heat exchange. Using the warming/cooling apparatus comprising the Peltier element as described above results in compactness of the bloodless treating apparatus, space saving, improved operability and so on.

The fluid replacement which leaves the fluid replacement temperature controller flows through a certain length of a conduit until supplied into the body, during which a temperature of the fluid replacement is affected by a temperature of its surrounding circumstance (i.e. a room temperature) so that the supplied fluid replacement temperature (T2) may be different from the temperature of the fluid replacement upon leaving the fluid replacement temperature controller (T3). For example, when the surrounding temperature is higher than the temperature of the fluid replacement upon leaving the fluid replacement temperature controller (T3), T2 is higher than T3, and when the surrounding temperature is lower, T2 is lower than T3. Therefore, it is usually possible that a substantive temperature difference $\Delta T$ ($=T3-T2$) is present. In the present apparatus, it is preferable to take this temperature difference $\Delta T$ into account when the fluid replacement temperature is adjusted based on the different extent between the withdrawn fluid replacement temperature (T1) and the predetermined temperature (T0) of the object. That is, in a preferable embodiment according to the present invention, the temperature of the fluid replacement temperature controller (T3) is controlled considering the temperature change of the fluid replacement between leaving the fluid replacement temperature controller and going into the body, namely the heat absorption from or the heat radiation into the surrounding circumstance of the apparatus.

Usually, the temperature difference is affected by parameters such as operation conditions of the apparatus (for example, a kind of the fluid replacement and its supply rate, a material of the conduit for supplying the fluid replacement and a diameter of the conduit), the temperature of the circumstance surrounding the apparatus (i.e. a room temperature, T4) and so on. Therefore, when relationships between the temperature difference $\Delta T$ and the parameters have been obtained beforehand as calibration curves by varying the parameters variously, it can be seen which temperature should be set in the fluid replacement temperature controller (T3) so as to achieve an aimed T2 under specific parameter conditions. Since T2=T0 is generally preferable at the beginning stage of the operation, T3 may be obtained based on the temperature difference between the T2(=T0) and T1.

Particularly, in the apparatus according to the present invention in which the withdrawn fluid replacement temperature (T1) and the supplied fluid replacement temperature (T2) are measured, the average of these temperature is assumed to be the object temperature, the different extent between the average and T0 is considered, and T2 is selected such that the different extent becomes smaller. Upon such selection, the temperature difference (ΔT) is considered and the set temperature of the fluid replacement temperature controller (T3) can be selected (=T2+ΔT), so that the temperature (T2) can be precisely controlled.

That is, since the withdrawn fluid replacement temperature (T1) is measured and the predetermined temperature of the object (T0) is determined beforehand depending on the treatment, the temperature which should be selected as T2 is obtained by T2=2T0−T1 for example if the averaged temperature of T1 and T2 is used as the temperature of the object. Further, ΔT can be obtained with reference to the calibration curves which were obtained under the specific parameter conditions as described above, and the set temperature of the fluid replacement temperature controller (T3) may be obtained by T3=T2+ΔT considering the ΔT with respect to the obtained T2, and the fluid replacement temperature controller is set at thus obtained T3.

In order to obtain a temperature of a liquid which is flowing through a length of a conduit while considering the heat transfer to its surrounding circumstance, various model equations are conceivable, and any model equation may be used as far as it does not substantially adversely affect works of the applied surgical treatment. Concretely, the following model equation for example may be used in place of the calibration curves as described above, so that the heat transfer between the liquid and its surrounding circumstance is considered so as to obtain the set temperature of the fluid replacement temperature controller (T3):

$$T3 = T2 - a \int_0^{l/v} (T4 - Tt) t \, dt \quad \text{Equation (I):}$$

(wherein l(l) is a length (m) of the conduit between the fluid replacement temperature controller and a position at which the supplied fluid replacement temperature is measured, Tt is a temperature (° C.) of the fluid replacement at a time of t (s or second), v is a supply rate (linear velocity, m/s) of the fluid replacement, a=αA/V$_1$, α is a heat transfer coefficient (W/m$^2$K), A is a total surface area (m$^2$) of the conduit, and V is a volume (m$^3$) of the fluid replacement in the conduit). It is noted that Equation (I) has been obtained from a general equation of the heat transfer.

In one case, the fluid replacement temperature Tt may be regarded to change linearly while the fluid replacement flows from the fluid replacement temperature controller to the position at which the supplied fluid replacement temperature is measured. In such case, the fluid replacement temperature Tt can be expressed by the following equation:

$$Tt = T3 + t(T2 - T3)/(l/v)$$

By substituting this equation in the above integral expression equation followed by numerical calculation, the temperature of the fluid replacement controller (T3) may be obtained as to the aimed T2. Other equation which can express Tt may be similarly used so as to obtain the temperature of the fluid replacement controller (T3).

Alternatively, in place of the above Equation (I), the following equation (II) may be used:

$$T3 = T4 - (T4 - T2)e^{b/v} \quad \text{Equation (II)}$$

in which b=4αl/(ρdCp)

(wherein α is a heat transfer coefficient (W/m$^2$K) of a material of the conduit, l is a length (m) of a conduit between the fluid replacement temperature controller and the position at which the supplied fluid replacement temperature is measured, ρ is a specific gravity (kg/m$^3$) of the fluid replacement, d is an outer diameter (m) of the conduit, Cp is a specific heat capacity (J/kgK) of the fluid replacement, and v is a supply rate (linear velocity, m/s) of the fluid replacement)

This equation may be obtained by forming a differential equation which expresses that an amount of heat loss of the fluid replacement into its surrounding while the fluid replacement flows over a very small length is equivalent to an amount of heat gained by the surrounding, solving the differential equation and integrating using boundary conditions that the fluid replacement temperature is T3 and T2, when the length of the conduit is zero and 1, respectively. It is noted that those skilled in the art can derive this equation easily with reference to for example "Zukai: Dennetu-kogaku no Manabikata (Illustration: How to learn heat transfer engineering)" (1st edition, 8th printing, by N. Kitayama, published by Ohmsha (Tokyo), Jul. 20, 1989, pp 104–109).

When the supplied fluid replacement temperature (T2) is not measured, the heat transfer between the fluid replacement and the surrounding of the apparatus until the fluid replacement of which temperature has been adjusted is considered upon controlling the temperature of the fluid replacement to be supplied. That is, when the fluid replacement temperature which has been adjusted is expected to become increased upon the entry into the body, the fluid replacement is adjusted to be lower beforehand by such temperature increase (which is thus similar to ΔT). In the opposite case, the fluid replacement is adjusted to be higher beforehand by ΔT.

In one preferable embodiment, the apparatus according to the present invention comprises an artificial lung which can oxygenate (add oxygen to) the fluid replacement and/or the blood to be supplied into the body. The artificial lung may be of any kind of device which has a function to increase an amount of oxygen existing in the blood, the withdrawn fluid replacement or the supplied fluid replacement, so-called an oxygen addition function or an oxygenation function, and for example a membrane type artificial lung and a bubbling type artificial lung may be used. In a particularly preferable embodiment, the fluid replacement to be supplied is introduced to the artificial lung where it is oxygenated, and then supplied into the body.

In one of other preferable embodiments, when blood is contained in the withdrawn fluid replacement, the apparatus according to the present invention can supply autologous blood drawn from a patient to be treated and/or transfusion blood together with the fluid replacement into the blood vessel depending on an amount of the blood contained in the withdrawn fluid replacement so as to compensate for the loss of the blood. Upon such supply, the autologous blood and/or the transfusion blood is preferably introduced to the artificial lung where it is oxygenated. In other embodiment, it is possible to oxygenate by providing, in place of or in addition to such artificial lung, a chamber which holds a liquid such as the supplied fluid replacement, the autologous blood or the transfusion blood and by bubbling the liquid with oxygen (or air) while blowing it into the liquid.

In the apparatus of the present invention, the recovery of the blood by removing water from the withdrawn fluid replacement means that a hematocrit value of the blood recovered from the fluid replacement which is withdrawn from the body and contains the blood (thus which value is smaller than a hematocrit value of original blood (i.e. the normal blood) due to dilution of the blood with the fluid replacement) is relatively increased or substantially recovered to the original value, and concretely it is carried out by filtration or dialysis (including diafiltration) (hereinafter these are generically referred to as filtration treatment). The filtration treatment may be carried out by a blood filtration device or a dialysis device (including a diafiltration device) or the like which is generally used as an artificial kidney. In the apparatus according to the present invention, the blood after being recovered has a hematocrit value of at least about 70% of, preferably at least about 90% of, more preferably at least about 95% of and most preferably substantially the same as that of the normal blood.

When the dialysis device (or a dialyzer) is used for the recovery of the blood from the withdrawn fluid replacement in the apparatus of the present invention, there is an advantage that balance of electrolytes and/or nutrients of the patient to whom the bloodless treating method of the present invention is applied can be kept, or the balance which has been destroyed can be recovered since the electrolytes and/or the nutrients which are required by the body are contained in dialysate are transferred to the recovered blood from the dialysate and excessive electrolytes and/or waste products which are not required by the body are removed from the blood by the dialysate. Thus, the blood supply unit may be preferably a hemodialysis device (including a continuous hemodialysis (CHD) device), or a hemodiafiltration device (including a continuous hemodiafiltration (CHDF) device).

In fact, in one embodiment in which the apparatus according to the present invention is used, a normal hematocrit value of a normal person (about 40 to 50%) is diluted with the fluid replacement, and the hematocrit value may generally lowered to about 5 to 20%, for example about 7% when regarding whole of the withdrawn fluid replacement to be as blood, and such diluted hematocrit value is recovered up to about 30 to 50% after being recovered. Therefore, a hematocrit value recovery ratio (a hematocrit value after recovery to a normal hematocrit value) is about 0.7 to 1.00.

The present invention will be further explained hereinafter in detail with reference to the accompanying drawings.

FIG. 1 is a diagram (flow sheet) which schematically shows the bloodless treating apparatus of the present invention, which comprises (A) the fluid replacement supply unit comprising a fluid replacement container (8), a fluid replacement supply pump (1) (with functions of metering a pumping rate and its adjustment) which supplies the fluid replacement into an organ (24) as the object from the fluid replacement container (8), a fluid replacement temperature controller (3) and a drip chamber for fluid replacement (9), and the temperature of the fluid replacement (T2) which is supplied into the object (24) through a balloon catheter (10) is measured by a supplied fluid replacement temperature sensor (4).

Also, the shown apparatus comprises (B) a fluid replacement withdrawing unit, which comprises a fluid replacement withdrawal pump (5) which withdraws the fluid replacement from the object (17) as a part in the body (17), and the fluid replacement withdrawal pump supplies the fluid replacement into the tank (14). The fluid replacement may be disposed of in an appropriate manner or wasted as it is. The temperature of the withdrawn fluid replacement (T1) is measured by a withdrawn fluid replacement temperature sensor (20). It is noted that a fluid replacement bottle (22) is provided in the blood withdrawing unit so as to fill conduits and elements in the apparatus with the fluid replacement upon starting the apparatus operation. Appropriate conduits (such as a silicone tube, a polyvinyl chloride tube or the like, shown with thicker lines in the drawing) connect between those units or various elements which constitute the units, and catheters (10 and 11) are used for supplying the fluid replacement to the object and withdrawing the fluid replacement from the object.

In the fluid replacement supply unit (A), the fluid replacement supply pump (1) is one which can quantitatively inject into the body (17) the fluid replacement, for example, usually at 10 to 800 ml/min., preferably 50 to 500 ml/min. and more preferably 100 to 400 ml/min. A practical supply rate of the pump is appropriately selected within those ranges depending on a purpose of the treatment for the object. As the pump which can quantitatively deliver (thus meter) the fluid replacement as described, a roller pump may be exemplified which is often used for the delivery of blood. It is noted that in order to carry out the speedy temperature adjustment of the object, the supply rate is preferably relatively large, and for example a supply rate in the range 100 to 400 ml/min. is further preferably used (particularly in the case of a brain of an adult as the object). In place of the roller pump, a centrifugal pump may be used, wherein an appropriate flow rate control means such as a valve, an inverter function or the like is preferably combined.

The withdrawal of the fluid replacement is carried out by means of the fluid replacement withdrawal pump (5). This pump and a flow rate thereof may be substantially the same as those of the fluid replacement supply pump (1). However, if the withdrawn fluid replacement contains blood, it is preferable to use a pump which can additionally withdraw the fluid by an excessive amount of the blood. The flow rates of the fluid replacement supply pump (1) and the fluid replacement withdrawal pump (5) may be different or the same, and these pumps are operated by a controller (19) such that a total amount of the supplied fluid replacement and that of the withdrawn fluid replacement (or an amount excluding the blood when the withdrawn fluid replacement contains the blood) are almost or substantially the same so as to avoid the excessive overhydration of the body. The withdrawal of the fluid replacement is not necessarily carried out from the starting of the supply of the fluid replacement, and the withdrawal of the fluid replacement is usually carried out after a predetermined period from the beginning of the supply of the fluid replacement has passed. Further, the withdrawal of the fluid replacement is not necessarily stopped immediately at the end of the supply of the fluid replacement, and the withdrawal of the fluid replacement is usually stopped after a predetermined period from the end of the supply of the fluid replacement has passed.

When the supply rate of the fluid replacement is controlled by for example a motor rotational speed of the fluid replacement pump (1), a flow meter is not necessarily provided as an additional element, but it may be located in a conduit for the fluid replacement so as to confirm the supply rate of the fluid replacement. The flow meter may be for example an electromagnetic flow meter. Further, the pump preferably has a control function which makes the supply rate as predetermined when it is not so (for example, a function to change the rotational speed of the pump motor (such as an inverter function) or a function to change a pressure loss of a conduit (such as a valve)). When the quantitative supply of the fluid replacement pump (1) is ensured, the flow meter may be omitted, and in this sense, the apparatus shown in the drawing has no flow meter.

Generally, a flow meter may be provided in any conduit through which a fluid has to be supplied at a predetermined flow rate, and combination of the flow meter with a pump ensures a predetermined flow rate (thus quantitative withdrawal or supply). As to the other pumps (5 and 7), the same as to the pump (1) is applicable except the flow rate ranges as described above.

The container (8) may be a plastic vessel or bag in which the fluid replacement is enclosed, or may be a bottle in which the fluid replacement taken out from such container is stored. There are provided the drip chamber (56) and a fluid empty detector (44) between the container (8) and the pump (1). The fluid replacement supply unit may further include in addition to the above described elements, other drip chamber (9, having a pressure gauge P) for the removal of bubbles, which removes the bubbles entrained with the fluid replacement if any. Similar drip chambers (12 and 16) are provided also in (C) a blood supply unit in a embodiment which is described below with referring to FIG. 2. It is noted that a filter (40) may be provided so as to remove contaminants in the fluid replacement and a bubble detector (42) may be provided for check the presence of the bubbles in the fluid replacement.

Figure 2:
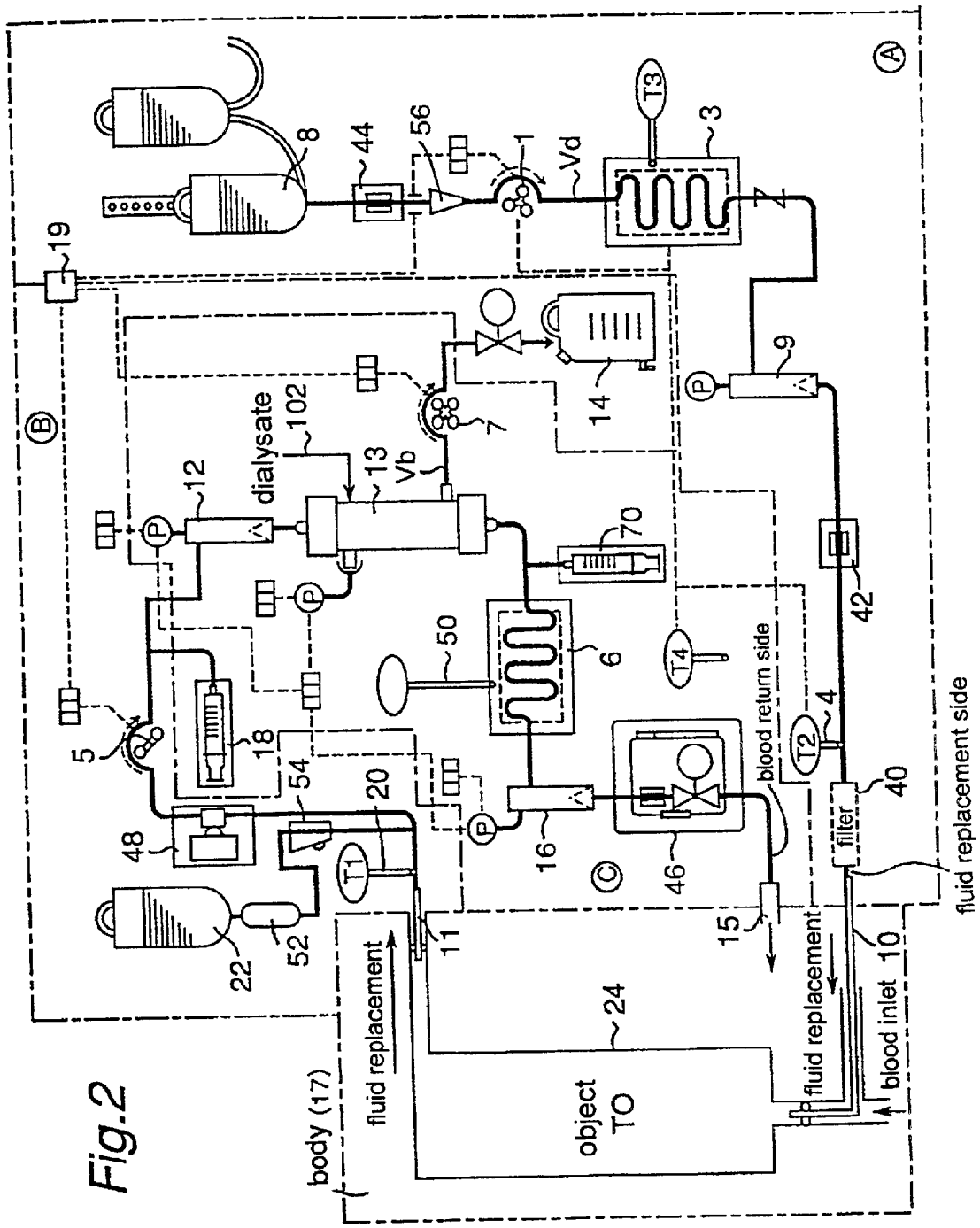
FIG. 2 is a schematic drawing which shows the bloodless treating apparatus in other embodiment of the present invention.

A diagram (flow sheet) of other embodiment of the bloodless treating apparatus according to the present invention is schematically shown in FIG. 2. In the shown embodiment, the apparatus further comprises (C) the blood supply unit in addition to the embodiment shown in FIG. 1, which unit recovers blood by removing water from the withdrawn fluid replacement, and returns the recovered blood into the body (17). The blood supply unit (C) transports the fluid replacement withdrawn from the object (24) to a blood recovery element (13) such as a hemofiltration device (or a diafiltration device) through the blood drip chamber (12) by an action of the fluid replacement withdrawal pump (5), and removes water contained in the fluid replacement into a removed water tank (14) at the blood recovery element (13) to recover the blood. The blood recovery element (13) optionally comprises a water removal pump (7), and the removed water is stored in the tank (14).

The blood recovered by the removal of the water is transferred through the heat exchanger (6) controlling the temperature of the blood and a blood return drip chamber (16) and returned to the body through other blood vessel. The heat exchanger (6) is provided with a temperature sensor (50) in order to control the temperature of the recovered blood. For passing the recovered blood through the heat exchanger (6) and returning it into the body, a discharge pressure of the fluid replacement withdrawal pump (5) can be used.

In FIG. 2 as similarly to FIG. 1, appropriate conduits (such as a silicone tube, a polyvinyl chloride tube or the like, shown with thicker lines in the drawing) connect between those units or various elements which constitute the units, and catheters (10 and 11 and 15) are used for supplying the fluid replacement to the object, withdrawing the fluid replacement from the object and returning the recovered blood into the body.

The apparatus of the present invention shown in FIG. 2 comprises the fluid replacement withdrawal pump (5) for quantitatively withdrawing the fluid replacement which has passed through the object as well as the element (13) for recovering the blood by removing water from the fluid replacement which has withdrawn and transferred to it. The pump (5) preferably quantitatively withdraws the fluid replacement through the catheter (11) at a rate in the range usually 10 to 600 ml/min., preferably 50 to 400 ml/min., and more preferably 80 to 300 ml/min. from the body. The practical flow rate of the pump (5) may be selected as required within such ranges depending on a purpose of the treatment. As the pump (5), one which is of the same type of that of the fluid replacement pump (1) may be used, and it may be cooperated with a flow meter (not shown) as described above.

Upon using the apparatus of the present invention shown in FIG. 2, the fluid replacement is withdrawn by means of the catheter (11) through a vein from the object, and it is introduced through the fluid replacement withdrawal pump (5) to an inlet for the fluid replacement of the blood recovery element (or a means for recovering the blood) (13) which is preferably a disposable product. In the apparatus of the present invention, the recovery element (13) is preferably a dialysis device (in which a dialysate (102) is supplied to the recovery element (13) as shown) or a filtration device, and the control of the element is preferably carried out based on the hematocrit values as measures before the blood is in a normal situation and after the blood is recovered. Measurement of the hematocrit value may be conducted by obtaining a volume percentage (%) of red blood cells after the recovered blood is subjected a centrifugation treatment.

It is convenient to measure a flow rate of the supplied fluid replacement and a flow rate of liquid discharged out from the recovery element (13) (which is also referred to as "filtrate") as well as a total amount of the fluid replacement which has been supplied and a total amount of the filtrate which has been discharged, and to control a patient not to be in an excessive overhydration condition or not to be in an excessive dehydration condition, and usually such control is sufficient. It is noted that when the dialysis device is used as the recovery element (13), an amount of the dialysate which has been supplied to the dialysis device is included in an amount of the filtrate, and thus such amount of the dialysate has to be deducted from the amount of the filtrate.

The recovery element (13) may include a pump (7) on its filtrate side when necessary, so that a pressure difference across the recovery element (13) can be further increased (and thus a controllable range of the filtration pressure (or a pressure difference upon the filtration operation) is enlarged), whereby a filtrate rate becomes more versatile due to using the pump (7). The recovery element (13) of course dehydrates by means of only the pressure difference produced by the pump (5) between the withdrawn fluid replacement side (a delivery pressure) and the permeate side (atmospheric pressure) produced by the pump (5), which is so-called natural filtration or natural dehydration (or water removal). In the case of the natural dehydration, the filtrate is collected in the filtrate container (14) without passing through the pump (7).

When the pump (1) is running, the filtrate rate from the recovery element (13) (Vb ml/min., provided that the supply rate of the dialysate is deducted from Vb in the case of the dialysis operation) is preferably substantially smaller than a supply rate of the fluid replacement supplied into the body (Vd ml/min.) so that a hematocrit value of the blood in the body is kept not higher than before the beginning of the bloodless treatment. This is based on an idea that in order to make the temperature adjusting effect by means of the apparatus of the present invention effective, it is preferable to temporarily keep a certain amount of the fluid replacement within the region of the object. Therefore, in a preferable embodiment of the apparatus according to the present invention, the flow rates are controlled to satisfy the relationship of $0.1Vd \leq Vb \leq Vd$ (wherein $Vd \neq 0$). When Vb is smaller than 0.1Vd (i.e. Vb<0.1Vd), an amount of the body fluid is considerably excessive temporarily, which is not preferable. On the other hand, when Vb is substantially larger than Vd, body fluid is excessively reduced from the object, which is not preferable. However, Vb being larger than Vd is not completely excluded in the apparatus of the present invention, and Vb may be larger than Vd if no adverse effect occurs in the treatment where the apparatus of the present invention is used.

In the apparatus of the present invention, the fluid replacement may comprise an aqueous solution comprising a low molecular material (such as an electrolyte, a saccharide (for example glucose)) as a main component in many cases. A total amount of the filtrate (provided that an amount of the dialysate is deducted from Vb in the case of the dialysis device as the recovery element) during the operation of the apparatus of the present invention is most preferably substantially the same as a total amount of the fluid replacement which has been supplied during the operation, which means under the consideration of the preferable relationship of $0.1Vd \leq Vb \leq Vd$ as described above that operation periods of the pump (1) and the pump (5) and optionally the pump (7) may be different, and that even though the pump (1) is being stopped, the pump (5) may be being operated so that Vb is a some substantive rate. The total amount of the filtrate (provided that an amount of the dialysate is deducted from Vb in the case of the dialysis device as the recovery element) is not necessarily substantially the same as the total amount of the supplied fluid replacement, and these amounts may be different as far as no problem occurs during the treatment. From such viewpoint, it is generally sufficient to keep a relationship of for example 0.8×total amount of filtrate (provided that an amount of the dialysate is deducted from Vb in the case of the dialysis device as the recovery element)≦total amount of supplied fluid replacement (provided that an amount of the dialysate is deducted from Vb in the case of the dialysis device as the recovery element)≦1.2×total amount of filtrate (provided that an amount of the dialysate is deducted from Vb in the case of the dialysis device as the recovery element). Since a certain period is required for the fluid replacement to be discharged after passing the object, the pumps (5) and (7) of course do not have to be started simultaneously with the operation start of the pump (1). It is noted that during a practical treatment or remedy, the supplied fluid replacement may be discharged as urine, which is included by the total amount of the filtrate in the present specification. That is, the urine is regarded to be the filtrate and the above relationship is considered (provided that a rate of the urine is not included in the filtrate rate Vb).

In the shown embodiment of the apparatus, the fluid replacement withdrawal pump (5) has a function to withdraw the fluid replacement from the object (24), a function to supply the fluid replacement to the recovery element (13) so as to allow the removal of the water and a function to return the recovered blood to the body (17) thereafter. It is obvious for those skilled in the art that these functions may also be achieved by separate pumps while providing buffers (or reservoirs) in-between.

The blood supply unit of the apparatus of the present invention may include the drip chamber (12) for the removal of bubbles and the anticoagulant supply element (18), for example a heparin supply device to prevent coagulation of the recovered blood by supplying heparin. It is noted that the anticoagulant (for example, heparin, futhan (i.e. nafamostat mesilate) or the like) may supplied at any other suitable position in the apparatus of the present invention. In the shown embodiment, the heparin supply device (18) is located in the blood supply unit, and the supplied heparin does not substantially transfer to the filtrate even though it passes through the blood recovery element (13) (namely, remaining in the recovered blood).

The apparatus of the present invention comprises the blood supply unit which adjusts the temperature of the recovered blood which may be at a higher or lower temperature to around the body temperature, and supplies such blood into a blood vessel (vein). Concretely, the unit comprises a heat exchanger for warming/cooling (6) which may be able to adjust the recovered blood to around 37° C. and supply it to usually a vein at a position which is closer to the heart. In the concrete, upon using the apparatus according to the present invention, the recovered blood passes the heat exchanger (6) by way of a conduit which is connected to an blood outlet of the blood recovery element (13), and injected into the vein through the catheter (15). In this case, there may be provided a protamine supply pump (70) (for neutralization of the heparin), a drip chamber for bubble removal (16) and a bubble detector (46).

In a preferable embodiment of the present invention, a supply/removal (dehydration) control mechanism (19) is provided which automatically controls each of the flow rate of the supplied fluid replacement Vd, the flow rate of the withdrawn fluid replacement, and the flow rate of the filtrate Vb so as to keep a body fluid amount as desired based on the balance of the flow rates. When the urine is discharged, the control of the balance may be carried out while considering an amount of the urine. When the supply/removal control mechanism (19) is used in the apparatus of the present invention, the flow rate of the supplied fluid replacement into the blood vessel, the flow rate of the withdrawn blood from the blood vessel, and the flow rate of the filtrate (thus, delivery rates of the pumps (1), (5) and (7), provided that the delivery rate of the pump (7) includes a rate of the dialysate in the case of the dialysis device as the recovery element) should have to be in controlled conditions along with a purpose of the treatment in which the apparatus is used. That is, the pumps (1) and (5) and optionally the pump (7) should be cooperated as shown with the broken lines such that Vb and Vd satisfy the ranges for them as described above, and the relationship between Vb and Vd as described above and the relationship between the total amount of the filtrate (provided that an amount of the dialysate is deducted in the case of the dialysis device as the recovery element) and the total amount of the supplied fluid replacement as described above are satisfied. Such control is well known to those skilled in the art and employed in an operation of an artificial kidney. It is noted that in place of the pump (7), other pump may be located on the recovered blood side of the blood recovery element (13) (i.e. downstream of the recovery element).

For example, it is not necessarily required that the filtrate of which amount corresponds to an amount of the supplied fluid replacement is immediately discharged. Of course, it may be possible that the filtrate is immediately discharged, but it is preferable that the fluid replacement is held in the body for a certain period, and then withdrawn gradually from the body so as to avoid the excessive overhydration of the body fluid. Vb and Vd are preferably controlled by the supply/removal control mechanism (19) so as to achieve such purpose.

Alternatively, hematocrit values of the withdrawn fluid replacement and/or the recovered blood are measured on line using a non-contact type hematocrit measuring device, and the supply/removal control mechanism (19) controls the flow rates of the pumps (1), (5) and (7) based on the measurements of the hematocrit values so as to keep the hematocrit value of the withdrawn fluid replacement for example not smaller than 5% and/or to keep the hematocrit value of the recovered blood for example at least 40%.

The bloodless treating apparatus of the present invention shown in FIG. 2 are possible to be used for controlling the temperature of the object for example as described below. It is noted that such control of the temperature is also similarly applicable to the apparatus shown in FIG. 1.

Case 1

Fluid replacement is charged beforehand from a fluid replacement bottle (22) into the elements and the conduits in the apparatus. First, a predetermined temperature (T0) to which the object is controlled and operation conditions such as a supplied fluid replacement rate, a withdrawn fluid replacement rate and so on are determined depending on an object (24) to which the surgical treatment is applied and the treatment for the object. Then, a heat exchanger (3) is operated, and its adjusting temperature (T3) is set at for example the predetermined temperature (T0). Upon this, the adjusting temperature (T3) may be shifted a little from the predetermined temperature (T0) considering the heat absorption or heat loss after leaving the heat exchanger (3) until entering the body (namely, $\Delta T$) as well as the temperature change after entering the body until reaching the object.

Each catheter is inserted into the blood vessel, and the pump (1) is operated and the fluid replacement is supplied from the fluid replacement tank (8) to the heat exchanger (3), whereby the fluid replacement temperature is adjusted to or near the predetermined temperature (T0) and then the fluid replacement is supplied into the blood vessel. Simultaneously or a predetermined period later, the pump (5) withdraws the fluid replacement from the blood vessel, and the temperature thereof (T1) is measured by by the temperature sensor (20). The withdrawn fluid replacement is supplied to the blood recovery element (13) where the blood is separated by means of filtration. Upon filtration, the dehydration (or water removal) pump (7) may be optionally operated so as to help the blood removal. The blood recovered by means of the filtration is passed through the heat exchanger (6) so as to heat to a temperature around the body temperature and then returned into the body through the catheter (15).

The above operation is carried out in the case where the measured withdrawn fluid replacement temperature (T1) may be regarded to represent an actual temperature of the region of the object, and thus the different extent between T1 and the predetermined temperature of the object region (T0), and for example the difference $\Delta Ta$ (=T1−T0) is obtained. When $\Delta Ta>0$, it means that the object has not been sufficiently cooled, and thus an operation to lower the set temperature (T3) of the heat exchanger (3) is carried out, which may be manually or automatically.

On the other hand, when $\Delta Ta<0$, it means that the temperature of the object has been excessively cooled, and an operation to raise the set temperature (T3) of the heat exchanger (3) is carried out. Thereafter, the withdrawn fluid replacement temperature is measured again, and $\Delta Ta$ is obtained similarly. Based on the obtained $\Delta Ta$, the set temperature (T3) of the heat exchanger (3) is changed. The time interval between the first calculation of $\Delta Ta$ and the second calculation of $\Delta Ta$ is not particularly limited, but when it is excessively long, the withdrawn fluid replacement temperature (T1) is likely to hunt, so that the interval is preferably short. It is of course possible that the withdrawn fluid replacement temperature (T1) is continuously measured, so that the set temperature (T3) of the heat exchanger (3) is considered while considering a characteristic of the temperature difference $\Delta Ta$ (such as an absolute value of the temperature difference, a change rate with time of the temperature difference or the like). The measurement and the change of the set temperature (T3) of the heat exchanger (3) as described above are repeated such that $\Delta Ta$ becomes smaller whereby the withdrawn fluid replacement temperature (T1) approaches the predetermined temperature of the object (T0) and such temperature is kept. It is noted that when $\Delta Ta$ is substantially zero, the set temperature (T3) of the heat exchanger (3) does not particularly have to be changed.

Case 2

Although in Case 1, only the withdrawn fluid replacement temperature (T1) is taken into account, the supplied fluid replacement temperature (T2) is also considered in addition to the withdrawn fluid replacement temperature (T1) in Case 2. In this case, the averaged temperature Tav of T1 and T2 (=(T1+T2)/2) may be regarded to indicate the actual temperature of the object (T0), and this case is generally superior in the estimation of the object temperature to Case 1 wherein only T1 is considered. Similarly to Case 1 described above, the different extent between the averaged temperature (Tav) and the predetermined temperature of the object region (T0), for example the difference $\Delta Tb$ (=(T1−T2)/2−T0) is obtained. The others are substantially the same as those in Case 1. It is noted that T1 and T2 have the same weight in this case so as to obtain the averaged value, but it may be possible optionally to change their weights. For example, it is possible to use 1.5×T1 in place of T1, and 0.5×T2 in place of T2. Particularly since T1 is affected by the object temperature, it may be preferable that T2 is regarded to be heavier.

When $\Delta Tb>0$, it means that the object has not been sufficiently cooled, and thus an operation to lower the set temperature (T3) of the heat exchanger (3) is carried out. On the other hand, when $\Delta Tb<0$, it means that the object has been excessively cooled, and an operation to raise the set temperature (T3) of the heat exchanger (3) is carried out. Thereafter, similarly to Case 1, the measurement is repeated, and Tav is made approach the temperature of the object (T0) so that $\Delta Tb$ is made approach zero and such condition is kept.

Case 3

Temperature adjustment of the heat exchanger (3) may be carried out in various appropriate manners depending on the different extent, for example the value of the difference $\Delta Ta$ or $\Delta Tb$.

For example, when the difference $\Delta Ta$ is positive in Case 1, the set temperature of the heat exchanger (3) is operated to be lowered so that the withdrawn fluid replacement temperature (T1) is decreased. When the difference $\Delta Ta$ is negative, the opposite operation is carried out. Upon these operations, it is preferable to consider a static characteristic and/or a dynamic characteristic of the difference $\Delta Ta$.

For example, when the difference $\Delta Tb$ is positive in Case 2, the set temperature of the heat exchanger (3) is operated to be lowered so that the supplied fluid replacement temperature (T2) is decreased. Upon this operation, considering that the difference $\Delta Tb$ desirably becomes zero, T2 is calculated from the predetermined temperature (T0) and the measured withdrawn fluid replacement temperature through an equation: T2=2T0−T1. The calculated T2 is used as the set temperature of the heat exchanger (3). In other embodiment, the set temperature (T3) of the heat exchanger (3) is determined based on the calculated T2 through the calibration curves or the above equation (I) under consideration of the heat exchange of the fluid replacement with the surrounding from the heat exchanger (3) to the temperature measurement position of the supplied fluid replacement. As seen from the equation, T3 varies depending on v. Depending on the surgical treatment, v is usually not an arbitrary value, but has been determined beforehand within an acceptable range. Therefore, the acceptable value of v is preferentially determined, and then T3 is finally determined.

Upon using the apparatus of the present invention, the fluid replacement flows from its container (8) through the supply pump (1) to the heat exchanger (3) for the fluid replacement temperature adjustment where its temperature is adjusted, and then supplied by means of the catheter (10) into the object (24) through a blood vessel leading to the object to which the surgical treatment is applied, which blood vessel is usually a blood vessel on an artery side of the object. It is noted that it may be possible to employ a method such as a so-called Seldinger's method with which a catheter is percutaneously inserted into for example a femoral artery up to an organ as the object so as to approach the object as close as possible followed by supplying or withdrawing the fluid replacement.

In such case, it is preferable not to locate the supplied fluid replacement temperature sensor (4) outside the body but to locate it at a tip or vicinity thereof of a leading end of the inserted catheter (10), so that a temperature of the supplied fluid replacement (T2') may be measured at a position which is closer to the object (i.e. at a more distal position). As a result, T2' is used in place of T2 which is used for the estimation of the temperature of the object in Case 2 described above. Similarly, as to the withdrawal of the fluid replacement from the object, the leading end of the catheter is inserted as close to the object as possible and the temperature sensor is located at a tip or vicinity thereof of a leading end of the catheter, so that a temperature of the fluid replacement withdrawn from the object (T1') can be measured at a position which is closer to the object.

Therefore, by locating the temperature sensor at the tip of the leading end of the inserted catheter, accuracy of the estimation of the object temperature is further improved, so that the surgical treatment can be effectively carried out. That is, T1' is used in place of T1 in Case 1, and T1' and T2' are used in place of T1 and T2 in Case 2, so that the temperature estimation of the object is further reliable. It is noted that an embodiment involving T1' and T2' is schematically shown in FIG. 5.

In the embodiment shown in FIG. 1 or FIG. 2, a pressure measuring element (48) for the withdrawn fluid replacement pressure is located before the pump (5), and a drip chamber (52) and a cramp (54) are located downstream of the fluid replacement bottle (22).

In a preferable embodiment, the bloodless treating apparatus of the present invention further comprises an artificial lung which oxygenates the fluid replacement, the autologous blood and/or the transfusion blood.

In the embodiment shown in FIG. 3, autologous blood obtained beforehand from a patient to be treated and/or transfusion blood (31) is supplied to the body through the artificial lung (28). FIG. 3 shows only a portion which is different from that of FIG. 1 or FIG. 2. The autologous blood or the transfusion blood (31) is passed to the artificial lung (28) through a liquid empty detector (62) and a drip chamber (64) by a pump (30), and thereafter merged to the fluid replacement which is freshly supplied, followed by passing through the heat exchanger (3) and thereafter to the body (17).

In the embodiment shown in FIG. 4, the fluid replacement which is to be supplied to the body is supplied to the artificial lung (28) after it leaves the heat exchanger (3), followed by passing to the body. It is noted that the configurations other than that shown in FIG. 4 are substantially the same as those in FIG. 1 or FIG. 2.

In addition to or in place of the artificial lung as described above, it is possible that oxygen gas is supplied to a drip chamber (9) which is located before the body after the heat exchanger (3) in a supply line for the fluid replacement, so that oxygen is bubbled in the fluid replacement (which may optionally include the autologous blood or the transfusion blood as described above) passing through the drip chamber so as to oxygenate it.

EFFECTS OF THE INVENTION

By using any of the embodiments of the apparatus or method according to the present invention, the surgical treatment can be applied with a minimized bleeding amount while the object to which the surgical treatment is applied is kept in a desired temperature condition with an improved accuracy. Particularly, when the position for the temperature measurement is close to the object, namely the temperature measurement is carried out most closely to the body, the accuracy is further improved. Especially, when the temperature sensor is located at around the leading tip of the catheter which is inserted into the blood vessel, the accuracy becomes remarkable.

In the case in which the surgical treatment is applied to the object by means of the apparatus of the present invention, the fluid replacement can be supplied preferably substantially only to the object. Therefore, even when it was difficult to apply the effective surgical treatment especially due to a large bleeding amount hitherto, the surgical treatment can be effectively applied since the bleeding amount is substantially reduced.

What is claimed is:

1. A bloodless treating apparatus used for a surgical treatment of an object, comprising:
    (A) a fluid replacement supply unit which quantitatively supplies a fluid replacement into a first blood vessel leading to the object, comprising:
        a supplied fluid replacement temperature sensor which measures a temperature of the supplied fluid replacement; and
        a means for controlling a temperature of the fluid replacement to be supplied based on a different extent between:
            (1) an averaged temperature of the measured supplied fluid replacement temperature;
            (2) the measured withdrawn fluid replacement temperature; and
            (3) the predetermined temperature of the object;
    (B) a fluid replacement withdrawing unit which quantitatively withdraws the fluid replacement from a second blood vessel coming from the object, after the fluid replacement passed through the object, comprising:
        a withdrawn fluid replacement temperature sensor which measures a temperature of the withdrawn fluid replacement; and
    (C) a blood supply unit which recovers blood contained in the withdrawn fluid replacement, and controls a temperature of the recovered blood, which is supplied into a third blood vessel.

2. A method for reducing a bleeding amount upon a surgical treatment of an object, which method comprises the steps of:
    (A) quantitatively supplying a fluid replacement of which temperature has been adjusted into a blood vessel by means of a fluid replacement supply unit;

(B) controlling a temperature of the fluid replacement which is quantitatively supplied by the fluid replacement supply unit based on a different extent between:
  (1) an averaged temperature of the measured supplied fluid replacement temperature;
  (2) the measured withdrawn fluid replacement temperature; and
  (3) the predetermined temperature of the object;
(C) quantitatively withdrawing the fluid replacement from a blood vessel;
(D) measuring a temperature of the withdrawn fluid replacement by means of a fluid replacement withdrawing unit;
(E) recovering blood contained in the withdrawn fluid replacement; and
(F) returning the blood into the object via a blood vessel preferably after controlling a temperature of the recovered blood.

3. The apparatus according to claim 1, wherein the fluid replacement supply unit and the fluid replacement withdrawing unit each comprises a balloon catheter which is inserted into the blood vessel.

4. The apparatus according to claim 1, wherein the control of the temperature of the fluid replacement to be supplied is carried out considering heat transfer between the fluid replacement and a surrounding of the apparatus until the fluid replacement of which temperature has been adjusted is supplied into the blood vessel.

5. The apparatus according to claim 1, wherein the supplied fluid replacement is injected into the blood vessel through an artificial lung.

6. The apparatus according to claim 1, which comprises, a drip chamber into which oxygen is injected.

7. The apparatus according to claim 1, wherein the supplied fluid replacement temperature sensor is located at around an end portion of the catheter on a distal side thereof, and the withdrawn fluid replacement temperature is located at around an end portion of the catheter on a distal side thereof.

8. The apparatus according to claim 1, wherein the surgical treatment is an operation.

9. The method according to claim 2, wherein the steps are carried out using the apparatus according to claim 1.

* * * * *

UNITED STATES PATENT AND TRADEMARK OFFICE
CERTIFICATE OF CORRECTION

PATENT NO.     : 6,855,122 B1
DATED          : February 15, 2005
INVENTOR(S)    : Tomio Ohta et al.

It is certified that error appears in the above-identified patent and that said Letters Patent is hereby corrected as shown below:

Title page,
Item [54], Title, please delete "BLOODLESS TREATING DEVICE" and substitute with -- BLOODLESS TREATING APPARATUS --.

Signed and Sealed this

Twenty-fourth Day of May, 2005

JON W. DUDAS
*Director of the United States Patent and Trademark Office*